United States Patent [19]
Ellis et al.

[11] Patent Number: 5,968,059
[45] Date of Patent: *Oct. 19, 1999

[54] TRANSMYOCARDIAL REVASCULARIZATION CATHETER AND METHOD

[75] Inventors: Louis Ellis, St. Anthony; Gary L. Hendrickson, Big Lake, both of Minn.

[73] Assignee: SciMed Life Systems, Inc., Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/812,425

[22] Filed: Mar. 6, 1997

[51] Int. Cl.$^6$ ..................................................... A61B 17/32
[52] U.S. Cl. ........................................... 606/167; 128/898
[58] Field of Search ...................... 606/167, 170, 606/159, 166; 604/49, 51, 22; 128/898

[56] References Cited

U.S. PATENT DOCUMENTS

| | | | |
|---|---|---|---|
| 4,790,311 | 12/1988 | Ruiz | 128/303.1 |
| 4,896,671 | 1/1990 | Cunningham et al. | 128/642 |
| 5,047,026 | 9/1991 | Rydell | 606/48 |
| 5,093,877 | 3/1992 | Aita et al. | 385/34 |
| 5,358,485 | 10/1994 | Vance et al. | 606/169 |
| 5,364,393 | 11/1994 | Auth et al. | 606/34 |
| 5,370,675 | 12/1994 | Edwards et al. | 607/101 |
| 5,380,316 | 1/1995 | Aita et al. | 606/7 |
| 5,389,096 | 2/1995 | Aita et al. | 606/15 |
| 5,403,311 | 4/1995 | Abele et al. | 606/49 |
| 5,522,815 | 6/1996 | Durgin, Jr. et al. | 606/50 |
| 5,591,159 | 1/1997 | Taheri | 606/15 |
| 5,593,405 | 1/1997 | Osypka | 606/15 |
| 5,607,405 | 3/1997 | Decker et al. | 606/167 |
| 5,620,414 | 4/1997 | Campbell, Jr. | 606/167 |
| 5,672,174 | 9/1997 | Gough et al. | 606/41 |
| 5,681,308 | 10/1997 | Edwards et al. | 606/41 |
| 5,683,366 | 11/1997 | Eggers et al. | 604/114 |
| 5,697,882 | 12/1997 | Eggers et al. | 604/114 |
| 5,700,259 | 12/1997 | Negus et al. | 606/14 |
| 5,713,894 | 2/1998 | Murphy-Chutorian et al. | 606/15 |
| 5,725,521 | 3/1998 | Mueller | 606/7 |
| 5,725,523 | 3/1998 | Mueller | 606/15 |

FOREIGN PATENT DOCUMENTS

| | | |
|---|---|---|
| 296 09 350 U1 | 10/1996 | Germany. |
| 195 37 084 A1 | 4/1997 | Germany. |
| WO 96/35469 | 11/1996 | WIPO. |
| WO 96/39963 | 12/1996 | WIPO. |
| WO 97/29803 | 8/1997 | WIPO. |
| WO 97/32551 | 9/1997 | WIPO. |
| WO 97/44071 | 11/1997 | WIPO. |

OTHER PUBLICATIONS

M. L. Goldman et al., "Nonoperative Portacaval Shunt in Swine," *Investigative Radiology*, vol. 25, No. 5, May 1990, pp. 574–578.

Abstract entitled "Transventricular Revascularization by Laser", *Laser in Surgery and Medicine*, 1982, 1 page.

Abstract entitled "Analysis of Photoproducts, Free Radicals and Particulate Debris Generated During In–Vivo Argon Laser Myoplasty", *Lasers in Surgery and Medicine*, 1991, 1 page.

(List continued on next page.)

*Primary Examiner*—Michael Buiz
*Assistant Examiner*—Kevin Truong
*Attorney, Agent, or Firm*—Crompton, Seager & Tufte, LLC

[57] ABSTRACT

A transmyocardial revascularization catheter which includes an elongate drive shaft having a proximal end, a distal end and a longitudinal axis. The TMR catheter also includes a cutting tip disposed at the distal end of the shaft. The tip has a distally disposed cutting edge and a longitudinally extending lumen therethrough. A motor is coupled to the drive shaft for rotation of the cutting tip. The shaft defines a longitudinally extending lumen in fluid communication with the tip lumen.

5 Claims, 4 Drawing Sheets

OTHER PUBLICATIONS

Isner, J., "Right Ventricular Myocardial Infarction", *The Journal of the American Medical Association,* V259, N5, Feb. 5, 1988, 12 pages.

Abstract entitled "Proliferative Activity in Peripheral and Coronary Atherosclerotic Plaque . . . ", *J. Clin. Invest.,* Apr., 1993, 1 page.

A. Vineberg et al., "Creation of Intramyocardial Pathways to Channel Oxygenated Blood Between Ventricular Arteriolar Zones", *Canad. Med. Assoc. Journal,* Feb. 4, 1967, vol. 96, pp. 277–279.

A. Vineberg, M.D., "Results of 14 Years' Experience in the Surgical Treatment of Human Coronary Artery Insufficiency", *Canad. Med. Assoc. Journal,* Feb. 13, 1965, vol. 92, pp. 325–332.

A. Vineberg et al., "The Ivalon Sponge Procedure for Myocardial Revascularization", *Surgery,* vol. 47, No. 2, Feb., 1960, pp. 268–289.

A. Vineberg et al., "Investigative Surgery: Treatment of Acute Myocardial Infarction by Endocardial Resection", *Surgery,* vol. 57, No. 6, Jun., 1965, pp. 832–835.

P. Walter et al., "Treatment of Acute Myocardial Infarction by Transmural Blood Supply From the Ventricular Cavity", *Europ. Surg. Res.,* 3:130–138 (1971).

H.A. Khazei et al., "Myocardial Canalization: New Method of Myocardial Revascularization", *The Annals of Thoracic Surgery*, vol. 6, No. 2, Aug., 1968, pp. 163–171.

J. Hershey et al., "Transmyocardial Puncture Revascularization: a Possible Emergency Adjunct to Arterial Implant Surgery", *Geriatrics,* Mar., 1969, pp. 101–108.

Press Release dated Oct. 21, 1996, entitled "Doctors Demonstrate Proof of Blood Flow Through Open TMR Channels Created with PLC Systems . . . ", PLC Systems, Inc., 1 page.

Press Release dated Oct. 10, 1996, entitled "Texas Fieart Institute Presents Study Comparing the Use of CO2, Holmrum and Excimer Lasers for TMR", 1 page.

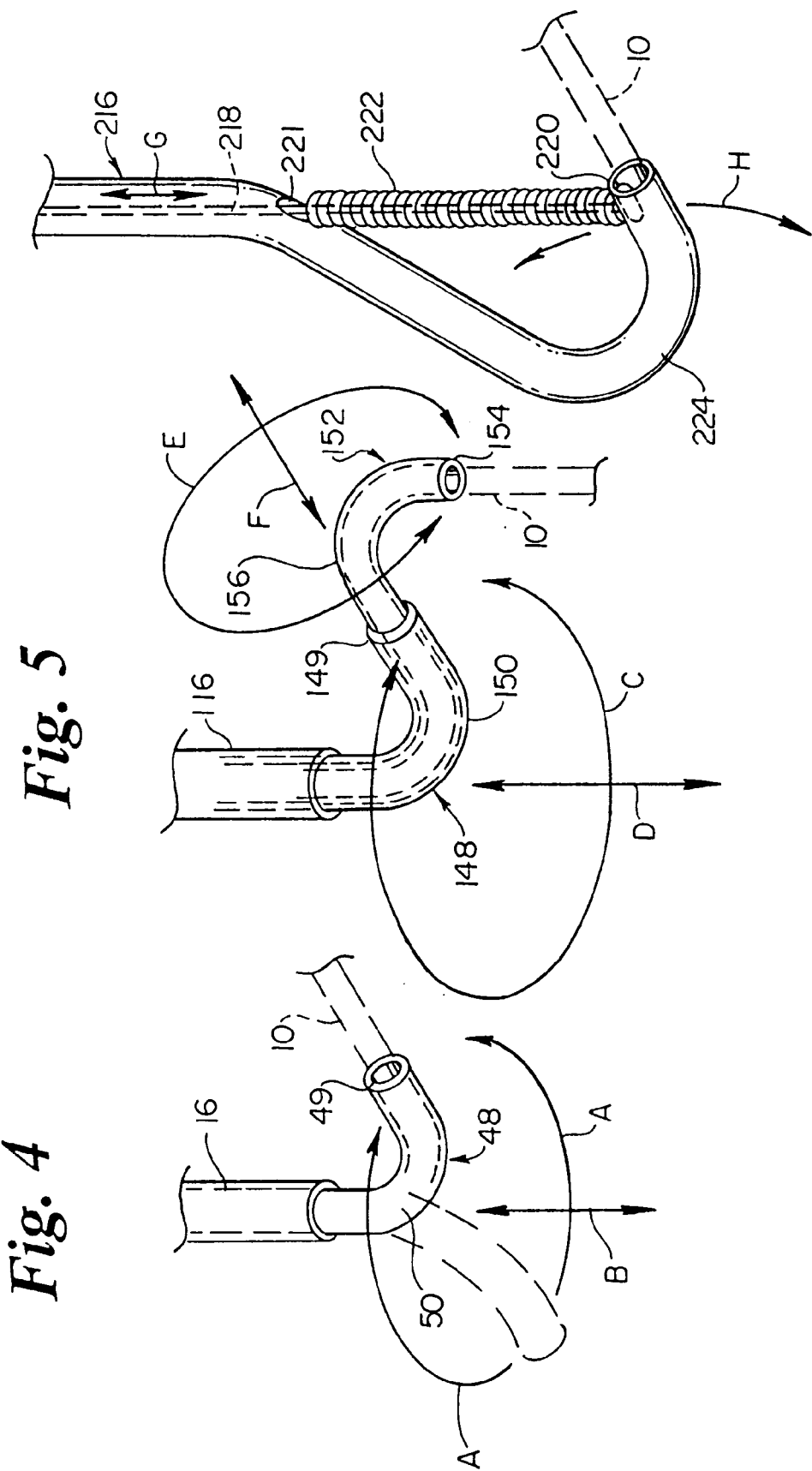

5,968,059

TRANSMYOCARDIAL REVASCULARIZATION CATHETER AND METHOD

FIELD OF THE INVENTION

The present invention pertains to the field of catheters and, in particular, to those having mechanical cutting tips.

BACKGROUND OF THE INVENTION

A number of techniques are available for treating cardiovascular disease such as cardiovascular by-pass surgery, coronary angioplasty, laser angioplasty and atherectomy. These techniques are generally applied to by-pass or open lesions in coronary vessels to restore and increase blood flow to the heart muscle. In some patients, the number of lesions are so great, or the location so remote in the patient vasculature that restoring blood flow to the heart muscle is difficult. Transmyocardial revascularization (TMR) has been developed as an alternative to these techniques which are directed at by-passing or removing lesions. TMR is performed by boring channels directly into the myocardium of the heart.

In one procedure, a laser catheter is advanced into the left ventricle. Laser radiation is then focused on the myocardium to create a channel. It has been found that creating several channels may be helpful. Lasers used to performed TMR can be costly and the depth of the channels can be difficult to control.

TMR has been performed by forming channels with laser energy as described above. TMR has also been performed by cutting a channel with a sharpened probe or blade. The channels cut by laser have a width proportional to the width of the focused laser radiation used to make the channels. When a laser is used, tissue is vaporized to form the channel, when the procedure is performed with a blade, tissue is not removed, but is merely pierced or cut.

Removing, or in the case of TMR laser techniques, vaporization of tissue is believed to enhance of the success of the TMR procedure. Removing tissue, however, by mechanical means has proved difficult.

SUMMARY OF THE INVENTION

The present invention pertains to an apparatus and method for performing TMR using a rotating cutting tip which has a lumen extending therethrough. The apparatus and method of the present invention provides a means for performing TMR by creating channels in the myocardium of the patient's heart which can vary in length and width. The depth of the channels is directly proportional to the distance which the cutting tip of the present invention is advanced into the patient's myocardium. The width of the channel can be varied by varying the diameter and width of the cutting tip.

A preferred embodiment of the TMR catheter in accordance with the present invention includes an elongate drive shaft having a proximal end, a distal end and a longitudinal axis. A cutting tip is disposed at the distal end of the shaft. The tip has a distally disposed cutting edge and longitudinally extending lumen therethrough. A motor is coupled to the drive shaft for rotation of the cutting tip.

The shaft can include a proximal portion and a distal portion, the distal portion being relatively more flexible than the proximal portion. The proximal portion can be a hypotube. The distal portion can include an elongate coil or elongate metallic braid reinforcing. The shaft can define a longitudinally extending lumen in fluid communication with the tip lumen. Dye or drugs may be infused through these lumens or fluid aspirated therethrough.

The cutting edge of the tip can be disposed at an acute angle to the longitudinal axis of the shaft. In such a case, the tip can be a hypodermic needle tip.

The TMR catheter can be used in conjunction with an elongate guide tube having a proximal end, distal end and a longitudinal axis. The guide tube defines a longitudinally extending lumen therethrough. The guide tube can include an inner tube and an outer tube longitudinally slidable with respect to each other. The inner tube and/or the outer tube can have curved distal ends. Each of the curves can extend approximately 60° to 120° from the longitudinal axis of the guide tube.

In the method in accordance with the present invention, the cutting edge of a TMR catheter, such as the one described above, while spinning, is advanced into engagement with the heart wall. (This helps to prevent the cutting edge from grabbing the tissue while it increases rpms.) Rotation of the tip will disintegrate the myocardium tissue through which the tip passes.

BRIEF DESCRIPTION OF THE DRAWINGS

FIG. 4 is a guide tube in accordance with the present invention;

FIG. 5 is an alternate embodiment of the guide tube in accordance with the present invention;

FIG. 6 is yet another alternate embodiment of the guide tube in accordance with the present invention.

DETAILED DESCRIPTION OF THE INVENTION

Figure 1:
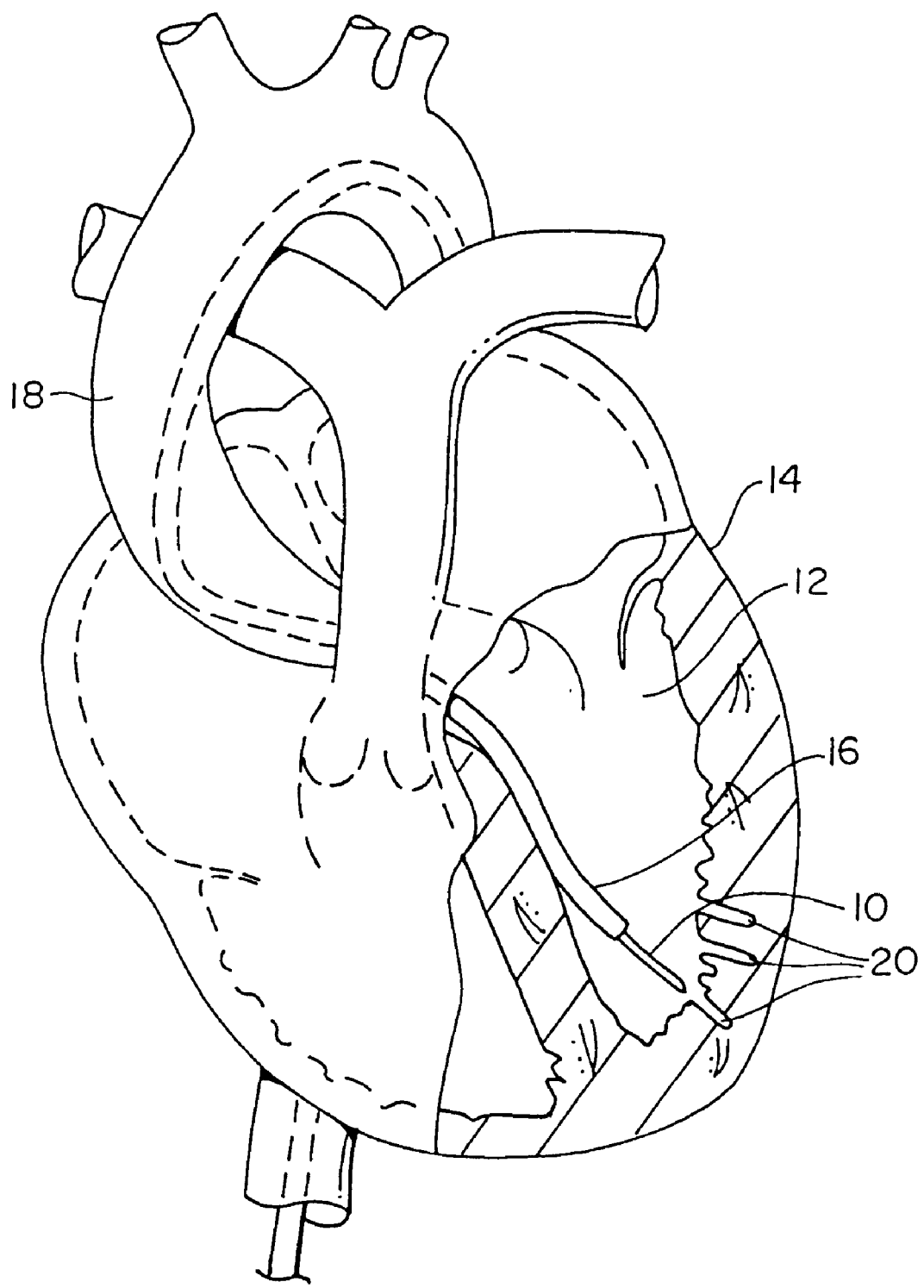
FIG. 1 is a view of a TMR catheter assembly in accordance with the present invention including a TMR catheter and guide tube within the left ventricle of the heart.

Referring now to the drawings wherein like reference numerals indicate like elements throughout the several views, a TMR catheter 10 in accordance with the present invention is shown in FIG. 1 within the left ventricle 12 of human heart 14. Catheter 10 is shown disposed within a guide tube 16 accessing left ventricle 12 through aorta 18. Channels 20 created by catheter 10 are shown in the myocardium.

Figure 2:
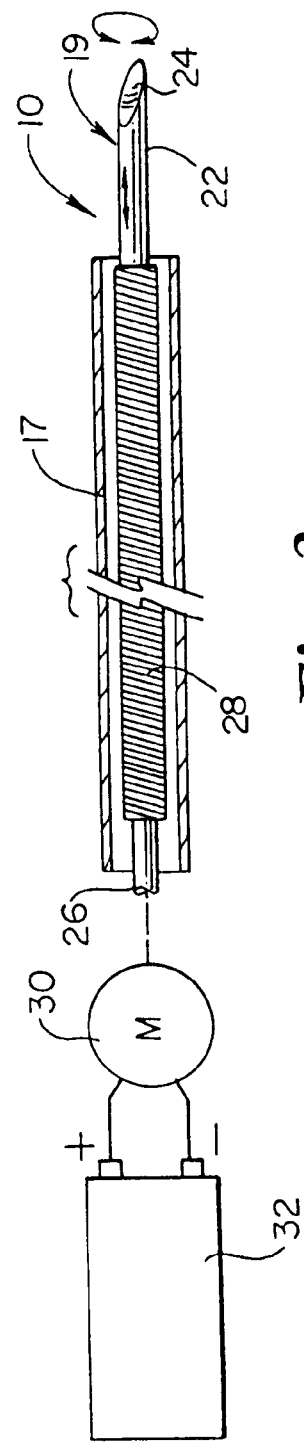
FIG. 2 is a partial cross sectional schematic side view of the TMR catheter in accordance with the present invention disposed within a guide tube.

FIG. 2 is a partial cross sectional schematic side view of catheter 10 including an outer shaft 17 and inner shaft 19. Inner shaft 19 preferably includes a distally disposed cutting tip 22. Having an opening 24 in fluid communication with a lumen through tip 24. Inner shaft 19 preferably includes a proximal shaft portion 26 and a more flexible distal shaft portion 28. Inner shaft 19 is connected to a motor 30 for rotation of inner shaft 19 about the longitudinal axis thereof relative to outer shaft 17 which is fixed against rotation. Motor 30 is connected to a power supply shown schematically as a battery 32. The spacing between outer shaft 17 and inner shaft 19 should be enough to allow sufficient rotation of inner shaft 19 relative to outer shaft 17. Inner shaft 19 is slidable longitudinally relative to outer shaft 17.

Figure 3:
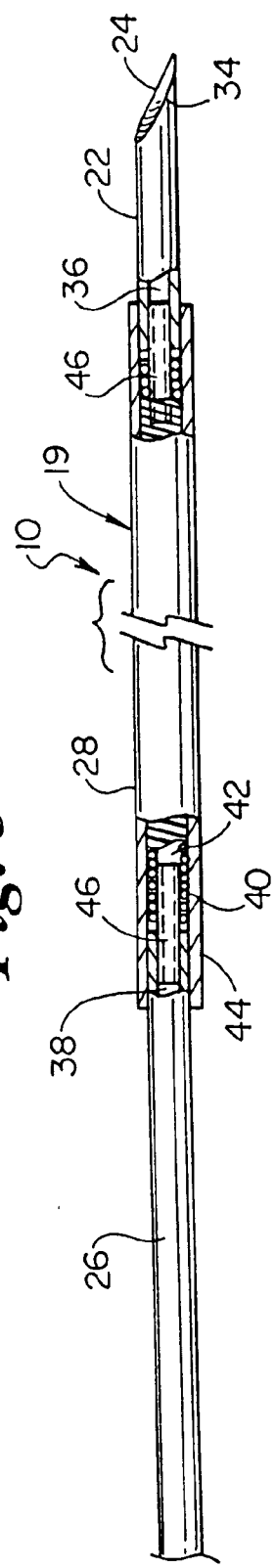
FIG. 3 is a partial cross sectional side view of the TMR catheter in accordance with the present invention.

FIG. 3 is a side and partial cross sectional view of inner shaft 19 of TMR catheter 10 shown schematically in FIG. 2. Cutting tip 22 which is preferably a hypodermic needle tip having a distally disposed cutting edge 34 at an acute angle to the longitudinal axis of inner shaft 19. Tip 22 defines a lumen 36 in fluid communication with opening 24. Although tip 22 is preferably formed from a hypodermic needle tip, it may be formed from other suitably durable and biocompatible materials as known to those skilled in the art. Tip 22 can have an outside diameter of, for example, 0.036 inches.

Proximal shaft 26 is preferably formed from a stainless steel hypotube which is more rigid than distal shaft 28. Shaft 26 defines a lumen 38 extending longitudinally therethrough. Proximal shaft 26 preferably extends the substantial majority of the length of inner shaft 19, to enhance the pushability and torqueability of inner shaft 19. It should be understood that although hypotube construction is preferred for proximal shaft 26, shaft 26 could be formed in the same manner as distal shaft 28 as described in more detail below or from another sufficiently torqueable and pushable construction as known in the art.

Distal shaft portion 28 is preferably more flexible than proximal shaft 26 to enhance trackability of inner shaft 19 proximate cutting tip 22. Distal shaft 28 can be formed from a helical coil 40 defining an elongate lumen 42 therethrough in fluid communication with lumen 38 of proximal shaft 26 and lumen 36 of cutting tip 22. Coil 40 can be surrounded by a polymer sheath 44. Sheath 44 may be PTFE, a shrink wrap or other similar biocompatible material known to those skilled in the art. The inside the coil forming the lumen wall of lumen 42 can be similarly coated. Shaft 28 can also be formed from superelastic alloy such as Nitinol.

Tip 22 and proximal shaft 26 can be connected to distal shaft 28 by two short tubular segments 46 and inserted within lumens 38 and 42, and 38 and 36, respectively. Tubular segments 46 can be small diameter hypotube segments or other sufficiently durable and biocompatible tubular members defining lumens in fluid communication with lumens 36, 38 and 42. An adhesive or braze can be used to bond segments 46 to shafts 26 and 28 and tip 22.

FIG. 4 is a view of a distal end of guide tube 16 for positioning catheter 10 and cutting tip 22 at various locations within heart 14. Guide tube 16 can include an inner tube 48 slidably and rotatably disposed therein. Tube 48 preferably has a distal end 49 and a distal curve 50. Curve 50 preferably extends approximately 90°. It should be understood that a greater or lesser curvature can be utilized, for example, between 60° and 120°. As shown in FIG. 4 by arrows A, tip 49 of tube 48 can be rotated 360° about the longitudinal axis of tube 48 disposed proximal of curve 50. As shown by arrow B, tube 48 may be drawn into or extended from tube 16. Tube 48 should be flexible enough such that as tube 48 is drawn into tube 16, curve 50 is straightened thus translating tip 48 through an angle equal to the angle through which curve 50 extends in an unconstrained state. Tubes 16 and 48 can be constructed from materials well known to those skilled in the art of catheters and, in particular, guide catheter construction.

FIG. 5 discloses an alternate embodiment of a guide tube 116. Extending from guide tube 116 is an inner tube 148 having a distal end 149 and a distal curve 150. In essential function and configuration, tube 148 is similar to tube 48 except that an additional tube 152 is disposed within tube 148. Like tube 48, tube 148 can be rotated about the longitudinal axis of the portion of tube 148 proximal curve 150 as shown by arrow C. Tube 148 also can be withdrawn into or extended from tube 116 as shown by arrow D.

Tube 152 has a distal end 154. Proximate distal end 154 is a curve 156. Curve 156 preferably extends through 90°, although other curves are within the scope of the present invention, including, for example, curves between 60° and 120°. As shown by arrow E, tube 152 and consequently, tip 154 can be rotated through 360°. Tube 152 can be withdrawn into or extended from tube 148 as shown by arrow F. Similar to tubes 48 and 148, tube 152 is sufficiently flexible that as it is withdrawn into tube 148, curve 156 will straighten such that tip 154 passes through an arch equal to the arc passed through by curve 156 in an unconstrained state. Those skilled in the art of catheter construction and, in particular, guide catheter construction will readily appreciate the techniques and materials available to construct the tubes 116, 148 and 152 in a manner which will function as described above.

FIG. 6 shows yet another embodiment of a guide tube 216 in accordance with the present invention. Guide tube 216 includes a distal end 220 connected to a tether 218. Tether 218 is disposed outside of tube 216 at distal end 220 and enters tube 216 at a proximally disposed opening 221, and then extends proximally to a proximal end of tube 216 where tether 218 is accessible to an operator. The portion of tether 218 disposed outside of tube 216 can be covered by an atraumatic accordion-like soft biocompatible sheath 222. Tube 216 includes a curved portion 224 proximate distal end 220. Curved portion 224 preferably is biased to straighten when unconstrained by tether 218. As shown by arrow G, tether 218 can be withdrawn into tube 216 or partially released therefrom. As shown by arrow H, drawing tether 218 into tube 216 or partially releasing it therefrom, will move tip 220, consequently changing the curvature of curve 224. Those skilled in the art of catheter construction and, in particular, guide catheter construction will readily recognize techniques and materials for constructing a catheter in accordance with catheter 216 described herein. Each of the tubes in FIGS. 4, 5 and 6 can advantageously include radiopaque markers at their distal ends.

Figure 7:
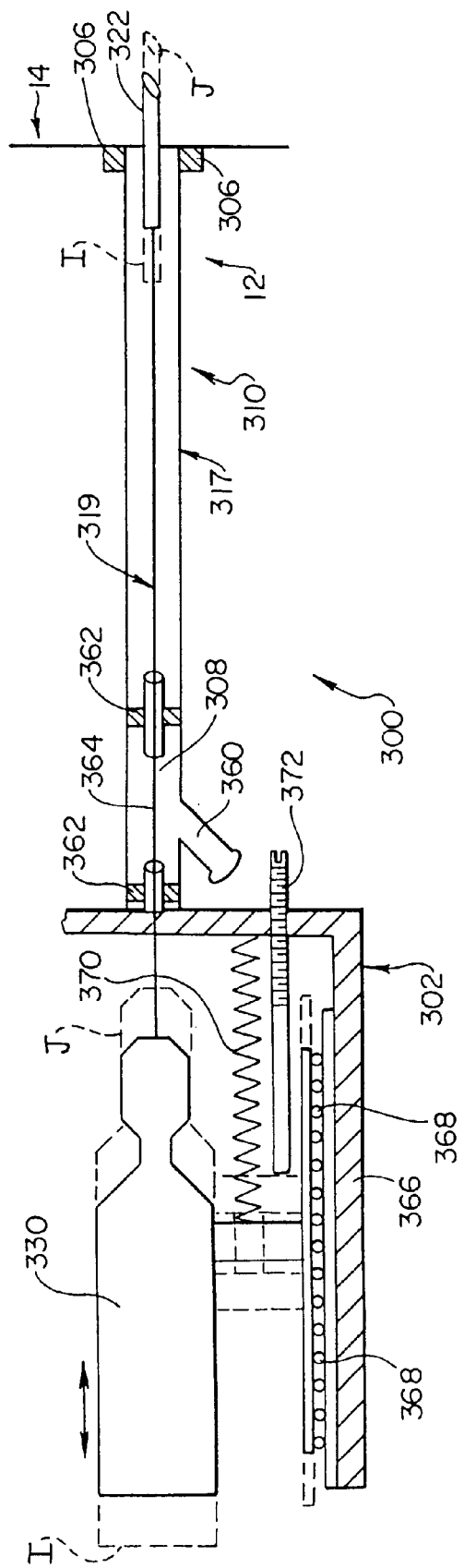
FIG. 7 is a motor drive and advancing apparatus in accordance with the present invention.

FIG. 7 is a longitudinal, cross-sectional view of a TMR advancer and catheter assembly 300. Assembly 300 includes a catheter assembly 310 having an outer shaft 317, an inner shaft 319 extending therethrough, and an advancer apparatus 302.

Outer shaft 317 includes a longitudinal lumen therethrough and a cutting tip 322 also having a longitudinal lumen extending in fluid communication with the longitudinal lumen of the portions of inner shaft 319 proximal thereof. This would be substantially similar to, for example, inner shaft 19 described above.

Outer shaft 317 is, in many respects, substantially similar to outer shaft 17 described above. As shown in FIG. 7, outer shaft 317 also includes radiopaque markers 306 at its distal end. At its proximal end is a manifold 308 having a port 360 sealed off from the remainder of catheter 316 by seals 362. Seals 362 can be close tolerance seals around catheter 310. Such seals, would allow rotation of inner shaft 319 relative to outer shaft 317. Port 360 is preferably in fluid communication with the longitudinal lumen through inner shaft 319 by apertures defined through inner shaft 319 within manifold 308 at 364 (in view of the scale of the drawing, the apertures are not visible). Disintegrated tissue or fluid can be aspirated through port 360 and inner shaft 319. Similarly, contrast medium or drugs may be introduced therethrough.

Advancer assembly 302 can include a frame or housing 366 connected to outer shaft 317, to hold outer shaft 317 against rotation. A motor 330 is interconnected to inner shaft 319 and mounted on frame 366 for longitudinal movement between a first position I and a second position J. As shown in FIG. 7, inner shaft 319 and motor 330 are in a position between positions I and J which are shown by broken line. In the embodiment shown, motor 330 is mounted on bearings 368 to enhance ease of movement between positions I and J. A spring 370 is provided to bias motor 330 and inner shaft 319 into position I. A set screw 372 is provided to limit distally position J. Preferably, the extreme distal tip of cutter 322 is contained within outer shaft 317 at position I. The amount of distal advancement of the extreme distal end of tip 322 at position J is proportional to the desired depth of the channel into the myocardium of heart 14.

Motor 330 rotates inner shaft 319 relative to outer shaft 319 which is held against rotation by housing 366. Motor 330 can be Dremel® motor having variable speed control between, for example, 3000 to 30,000 rpm. The motor can be run off of a battery or from a conventional AC plug-in.

In use, cutting tip 22 of inner shaft 19 can be delivered intravascularly to the heart wall and myocardium by catheter tube or tubes as, for example, shown in FIGS. 4–6 herein. It can be appreciated that the catheter as shown in those figures provides substantial flexibility for tip positioning. In fact, as can be appreciated in certain configurations tip positioning is possible at substantially all spherical coordinates. Once cutting tip 22 has been brought into contact with the heart wall, motor 30 can be activated to rotate cutting tip 22 and consequently blade 34. By further advancing cutting tip 22 into the myocardium of the heart, tissue in the path of the rotating blade will disintegrate. The disintegrated tissue can be aspirated through the lumens extending through inner shaft 19. Contrast medium or drugs may be introduced through inner shaft 19 as well. It can be appreciated that cutting tip 22 can penetrate the myocardium without being rotated. However, disintegration of tissue will generally not occur without rotating of tip 22.

Generally, the channel depth will be between ⅔ and ¾ the thickness of the heart wall. The specific channel depth will be determined on a case by case basis for each patient. Ultrasonic techniques may be used to view the patient's heart to determine the appropriate depth of the channels. The depth of the channels will be generally proportional to the depth of penetration of cutting tip 22 into the myocardium. The rotation rate of cutting tip 22 may vary upon the character of the heart tissue encountered but should be rapid enough to disintegrate the tissue in the path of the cutting tip.

Outer shaft 17 and 317 can also include hoods at their distal ends; outer shaft 17 and 317 could be formed at least in part by a coil having adjacent windings. The coil having adjacent windings would offer column strength as well as the enhancement to aiming described in the referenced application.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of performing transmyocardial revascularization, comprising the steps of:

providing a transmyocardial revascularization catheter including an elongate drive shaft having a proximal end, a distal end and a longitudinal axis; a cutting tip disposed at the distal end of the shaft, the tip having a distally disposed cutting edge and longitudinally extending lumen therethrough; and a motor coupled to the drive shaft for rotation of the cutting tip;

advancing the cutting edge of the tip into engagement with the heart wall;

rotating the tip; and advancing the tip into the myocardium of the heart.

2. The method of performing transmyocardial revascularization in accordance with claim 1, wherein the shaft of the catheter defines a longitudinal lumen in fluid communication with the tip lumen.

3. The method of performing transmyocardial revascularization in accordance with claim 2, further comprising the step of infusing a dye through the lumens.

4. The method of performing transmyocardial revascularization in accordance with claim 2, further comprising the step of infusing a drug through the lumens.

5. The method of performing transmyocardial revascularization in accordance with claim 2, further comprising the step of aspirating fluid through the lumens.

* * * * *